(12) United States Patent
Christman et al.

(10) Patent No.: US 9,140,685 B2
(45) Date of Patent: Sep. 22, 2015

(54) APPARATUS AND METHODS FOR TESTING APPARATUS INCLUDING ON-BOARD INSTRUCTIONAL VIDEOS AND UPLOAD/DOWNLOAD DATA CAPABILITIES

(75) Inventors: Norbert John Thomas Christman, Wauwatosa, WI (US); Katherine M. Ross, West Allis, WI (US)

(73) Assignee: QuinTron Instrument Company, Inc., Milwaukee, WI (US)

( * ) Notice: Subject to any disclaimer, the term of this patent is extended or adjusted under 35 U.S.C. 154(b) by 141 days.

(21) Appl. No.: 13/162,281

(22) Filed: Jun. 16, 2011

(65) Prior Publication Data

US 2012/0150056 A1     Jun. 14, 2012

Related U.S. Application Data

(60) Provisional application No. 61/397,865, filed on Jun. 17, 2010.

(51) Int. Cl.
*A61B 5/08*     (2006.01)
*G01N 33/497*     (2006.01)
*A61B 5/00*     (2006.01)

(52) U.S. Cl.
CPC .............. *G01N 33/497* (2013.01); *A61B 5/082* (2013.01); *A61B 5/4216* (2013.01); *A61B 5/7475* (2013.01)

(58) Field of Classification Search
USPC ........................................................ 600/532
See application file for complete search history.

(56) References Cited

U.S. PATENT DOCUMENTS

2007/0093725 A1*   4/2007   Shaw ............................ 600/543
2007/0273697 A1*   11/2007   Zaman et al. ................. 345/501
2011/0282228 A1*   11/2011   Shiner et al. .................. 600/534

OTHER PUBLICATIONS

Quintron Catalog and Information, copyright 2009.*
Catalog page, Quintron Instrument Compnany, Inc., "Basics of Hydrogen/Methane Breath Tests", p. 6, 1 page, dated 2009.

* cited by examiner

*Primary Examiner* — Michael Kahelin
*Assistant Examiner* — Mitchell E Alter
(74) *Attorney, Agent, or Firm* — Ryan Kromholz & Manion, S.C.

(57) ABSTRACT

A breath testing apparatus is provided with on-board "Instruction Manual" tutorials incorporated in a display device installed in the device. Alternatively, on-board instructional videos can be added to various objects or processes requiring instructions.

1 Claim, 7 Drawing Sheets

APPARATUS AND METHODS FOR TESTING APPARATUS INCLUDING ON-BOARD INSTRUCTIONAL VIDEOS AND UPLOAD/DOWNLOAD DATA CAPABILITIES

RELATED APPLICATIONS

This application claims the benefit of U.S. Provisional Patent Application Ser. No. 61/397,865, filed 17 Jun. 2010.

BACKGROUND OF THE INVENTION

This invention relates to the field of sampling air from the lungs and specifically to the field of obtaining a sample of a person's air, including alveolar air from the alveoli of the lungs of a person.

Air from the lungs of a person can be used for many different types of testing that would otherwise require the person to undergo an invasive procedure. For example, alveolar air can be analyzed for, but not limited to, the noninvasive diagnosis of a wide variety of conditions including the noninvasive diagnosis of stomach infections related to a high incidence of ulcers, enzymatic deficiencies, and metabolic conditions and/or abnormalities. Crucial to any such testing is the ability to get an accurate sample containing a sufficient volume of air representative of true alveolar air, necessary for specific testing.

Often times scientific testing apparatus' can be complicated, requiring a significant amount of user training and familiarity in order to master the operation of the apparatus and ensure consistent test results.

In the medical device industry, it is typically necessary to provide In-Service instruction for both operation and utilization of Medical Instrumentation. This requirement can be expensive and time-consuming for both manufacturer and users. Additionally, when personnel previously trained on the use of such instrumentation are transferred or otherwise leave the organization owning such devices, it is often common to have new users retrained by the manufacturer or the departing individual. This can prove problematic when the departing or departed individual is pressed into a hasty training session where time may not be sufficient for proper instruction. If a user requires re-training, or a new operator uses the machine, it is desirable to have a convenient training method to use.

Hydrogen and methane are produced in the digestive system primarily only by the bacterial fermentation of carbohydrates (sugars, starches or vegetable fibers), so if either of these gases appear in the expired air, it is usually a signal that carbohydrates or carbohydrate fragments have been exposed to bacteria, permitting such fermentation to take place. The generation of H2 and/or CH4 will result in the reabsorption of some of these gases into the blood stream from the site of their digestion, and they will appear in the expired air.

Bacteria are ordinarily not present in significant numbers in the small intestine, where digestion and absorption of sugars take place. Therefore, when a challenge dose (eg. lactose) is ingested, the level of hydrogen in alveolar air will rise significantly within one to two hours (depending on the intestinal transit time) only if the sugar is not digested and, therefore reaches the colon.

The breath-H2 test is a simple non-invasive procedure which is readily accepted by patients and staff, and which has greater reliability and acceptability than the blood test, according to many reports. The lower dose of lactose usually does not cause the discomfort and explosive diarrhea frequently seen by malabsorbers who are given the larger dose required for the blood test.

A study with over 300 patients showed that G-I symptoms after a lactose challenge are strongly associated with the amount of H2 excreted; the relationship between blood glucose change and symptom-severity was less evident.

False-positive breath-tests are rare, and when they occur they are usually caused by improperly doing the test—allowing the subject to smoke, sleep or eat shortly before or during the test. Bacterial overgrowth (from the colon retrograde into the small intestine) can also produce a false-positive breath-test, but it is usually preceded by an elevated fasting breath-H2 level and the response is seen soon after the sugar is ingested (within 20-30 minutes).

The incidence of false-negative results with the breath-test is well below that seen with the blood test. False-negative results are reported to be from 5-15% of all lactose malabsorbers, due to a variety of causes. Many of the false-negative reports can be avoided by measuring methane in addition to hydrogen because some methanogenic flora convert colonic H2 to CH4.

SUMMARY OF THE INVENTION

In accordance with the present invention, a testing apparatus is provided with intelligent on-board capabilities, including such things as "Instruction Manual" tutorials incorporated in a display device installed in the device is provided. Alternatively, on-board instructional videos can be added to various objects or processes requiring instructions. Exemplary uses of the present invention also include video displays in automobiles, which often incorporate combined GPS-DVD-CD-AM FM Radio consoles. Such video capabilities can be added to include commercially available video applications such as which could include a "flash player", HTML 5, MPEG, WMV, AVI, DIVX or other video player. In this embodiment, the present invention can be used to display video demonstrating the operation of certain devices in the auto such as, the location and method of changing the spare tire, and other pertinent demos related to operation of the vehicle or devices within the vehicle (setting the clock, etc). It could also include instruction manuals for repair and servicing. A similar enhancement of an existing function in automobiles would be the modification to windshield wipers to provide intermittent function for the wipers.

In another alternate embodiment of the present invention, video capability is added to machines such as computer printers, fax machines, and copiers often have lcd graphic displays for simple sequential operations of the devices. Adding video player functions would enhance the ability to provide more comprehensive instructions in the operation of the device.

In another alternate embodiment of the present invention, scientific and laboratory instruments are provided with "In Service" Instructions directly on those devices (in the form of video), ensuring proper training for successive users. These "In Service" instructions may result in significant savings for the manufacturer, by eliminating requirements for training personnel to travel to user sites to provide "In Service" training.

In another alternate embodiment of the present invention, inclusion of graphic display devices are provided to allow visual "Instruction Manuals" in many other types of vehicles such as snowmobiles, atvs, lawnmowers, motorcycles and other vehicles, to provide instruction on incorporated DVD players, televisions, stereo equipment.

In accordance with the present invention, a testing apparatus is provided with on-board "Instruction Manual" tutorials incorporated in a display device installed in the device. Alternatively, on-board instructional videos can be added to various objects or processes requiring instructions. Exemplary uses of the present invention also include video displays in automobiles, which often incorporate combined GPS-DVD-CD-AM FM Radio consoles. Such video capabilities can be added to include commercially available video applications such as which could include a "flash player", HTML 5, MPEG, WMV, AVI, DIVX or other video player. In this embodiment, the present invention can be used to display video demonstrating the operation of certain devices in the auto such as, the location and method of changing the spare tire, and other pertinent demos related to operation of the vehicle or devices within the vehicle (setting the clock, etc). It could also include instruction manuals for repair and servicing. A similar enhancement of an existing function in automobiles would be the modification to windshield wipers to provide intermittent function for the wipers.

In another alternate embodiment of the present invention, video capability is added to machines such as computer printers, fax machines, and copiers often have lcd graphic displays for simple sequential operations of the devices. Adding video player functions would enhance the ability to provide more comprehensive instructions in the operation of the device.

In another alternate embodiment of the present invention, scientific and laboratory instruments are provided with "In Service" Instructions directly on those devices (in the form of video), ensuring proper training for successive users. These "In Service" instructions may result in significant savings for the manufacturer, by eliminating requirements for training personnel to travel to user sites to provide "In Service" training.

In another alternate embodiment of the present invention, inclusion of graphic display devices are provided to allow visual "Instruction Manuals" in many other types of vehicles such as snowmobiles, atvs, lawnmowers, motorcycles and other vehicles, to provide instruction on incorporated DVD players, televisions, stereo equipment.

The device utilizes an existing product (7" Android tablet computer) as the User Interface and Control Device for an Instrument. A primary reason for this approach is that such devices have many built-in functions that can be utilized in providing an instrument with extremely diverse utility. Built-in capability to read PDF files, show video files, connect to wifi for email and internet access, bluetooth communications for control functions, programmability enabling incorporation of the designers proprietary functions and design are typical of the capability of such devices. Additionally the flexibility of this concept allows simple modification of the User Interface with additional push-button controls and displays as well as other control and information access. The Control Function of such a system can also be modified simply. Independently designing an instrument with all this functionality is certainly attainable; however design time and expense would most likely be long and excessive.

An instrument manufactured with Built-in video operation could prove invaluable where in-service training is available on the instrument itself. Additional Built-in pdf Reader capability would provide reference materials for training, supplies information, and part numbers, patient diet instructions and pretest options and requirements, prescription drug instructions, dosing instructions and tools if the test requires drug or other substrate ingestion or inoculation. Communications capabilities provide additional power in such a device. Wifi and Bluetooth communications and existing or available ethernet communications can provide a rich variety of options for communicating test results, patient appointment information, consultation options and general information sharing in many forms . . . SMS, MMS, Email, etc. Powerful calendars and other utility software designed as applications for the Android operating system (or other operating systems, such as Windows, Chrome, etc; if the primary system is an alternative O.S.) can provide an additional source of enhanced functionality to the Instrument. This design concept applies additional instrument design and control flexibility.

In another alternate embodiment of the present invention, small inexpensive electronic picture frames are provided as inclusions to various things requiring installation or assembly.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
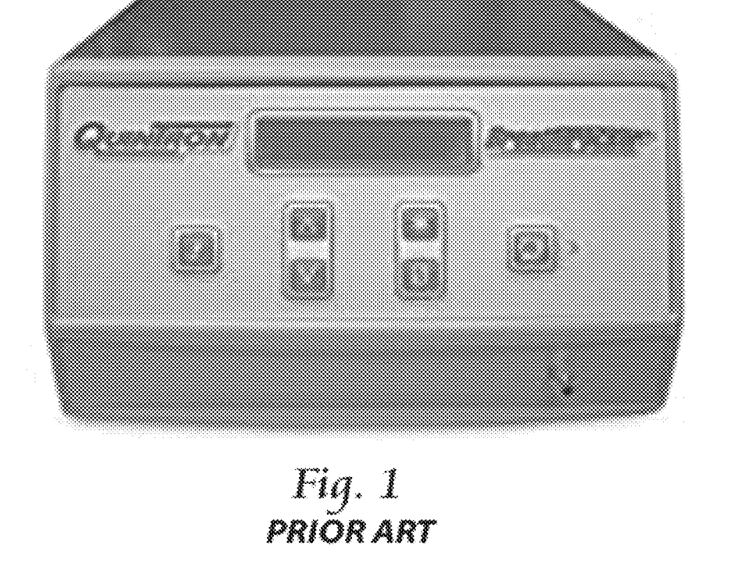
FIG. 1 is a front view of a breath testing machine of the prior art.

Referring now to FIG. 1, a prior art breath testing machine is shown. In the prior art, data was essentially limited to data display with some limited data output (e.g., USB cabling) to computers carried outboard to the breath testing machine. The same machine used to take the breath test was not well equipped to analyze or storing the data, or to display information such as instruction manuals or tutorial videos.

Studies have demonstrated the interaction of hydrogen and methane in carbohydrate malabsorption, small intestinal bacterial overgrowth and other digestive disturbances in some patients.

The instrument shown in FIG. 1 is the result of advancements original gas chromatography techniques developed to measure both H2 and CH4 in a single sample of alveolar air by the most simple, reliable and accurate method. The added feature of the instrument shown in FIG. 1 is its ability to calculate the alveolar concentrations of components in breath samples which may have been imperfectly collected or accidently contaminated by mishandling or transport. The teachings of U.S. application Ser. No. 12/456,814, owned by the common assignee of the present invention, is hereby incorporated by reference. The instrument generates a correction factor based on the degree of dilution of alveolar CO2 with dead space air or with inspired air during an improper collection procedure and applies it to the trace gas measurements.

Within 50 seconds after introducing the sample, the instrument shown in FIG. 1 displays sample H2 (Hydrogen), CH4 (Methane), and CO2 (Carbon Dioxide) concentrations on the alphanumeric backlit data display. Then, with the push of a button the instrument activates the correction feature and displays the correction factor (Alveolar CO2/Sample CO2) and the corrected values for H2 and CH4.

The instrument shown in FIG. 1 separates the components by the basic principle of gas chromatography, using room air as the carrier gas, which is pumped through the system by an internal circulating pump. Hydrogen and Methane are separated from all other reducing gases and from each other, and are carried past a solid-state sensor, which you won't find in the electrochemical (fuel sensor) portable devices in the field today. The sensors are affected only by reducing gases, so it is unaffected by other gases in the sample. The instruments of the present invention measure hydrogen and methane preferably from a single sample of alveolar air, increasing the accuracy of the breath test. An internal pump is supplied to flush out previous samples from the instrument.

Figure 2:
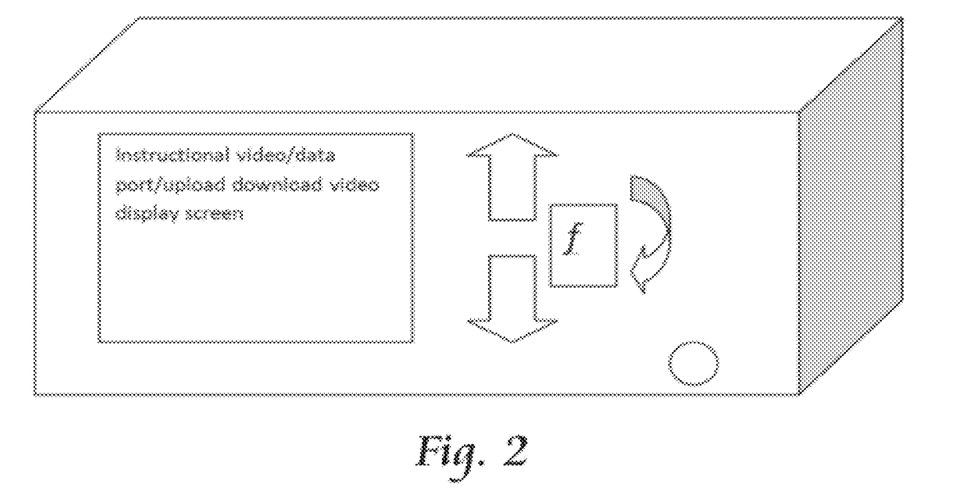
FIG. 2 is a schematic view of one embodiment of the present invention.

Referring now to FIG. 2, a schematic view of one embodiment of the present invention is shown. The onboard gas chromatograph components of the instrument shown in FIG. 1 are employed. As can be seen, an instructional video (prepared by the equipment supplier, and uploaded from either a remote or hard wired source) is provided along with the schematic user interface and controls that are common on scientific instrumentation. The instructional video teaches users how to use the machine, and can be provided with other instructional videos or displays as desired.

This is provided by a video screen (preferably touch screen) coupled to a microprocessor; coupled to the gas chromatograph. Preferably, a data port and upload/download capabilities are provided on the instrument, cooperative with the video display screen. In this manner, updated video display can be downloaded from the internet, and data can be uploaded to the internet via techniques such as wireless connectivity and USB cabling. In other embodiments, other upload/download capabilities are provided which can be tailored according the user preferences or as the desired situation requires. Other types of connectivity, such as wireless or machine-to-machine connectivity can be supplied.

Figure 3:
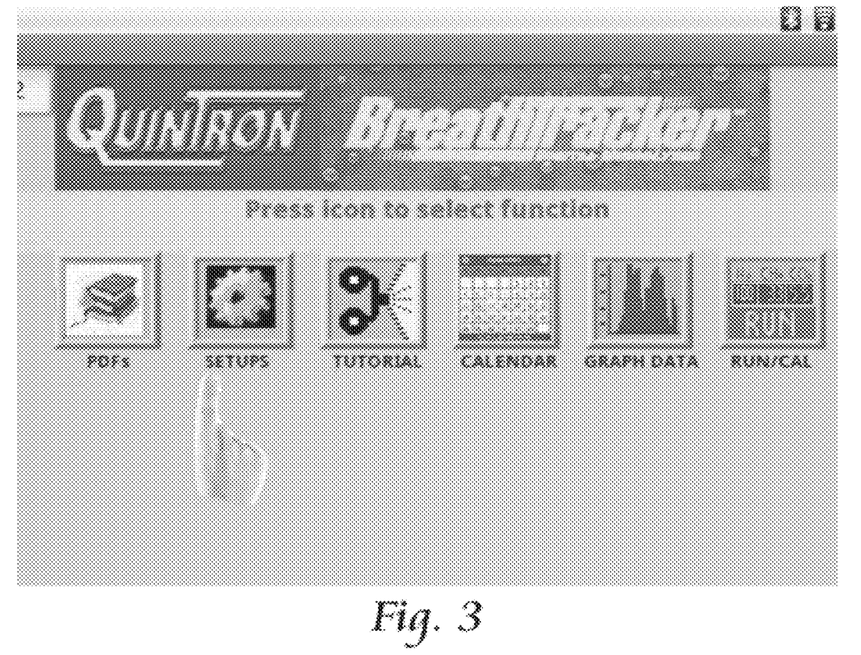
FIG. 3 is an exemplary screen shot of a user interface showing a main screen.
Figure 7:
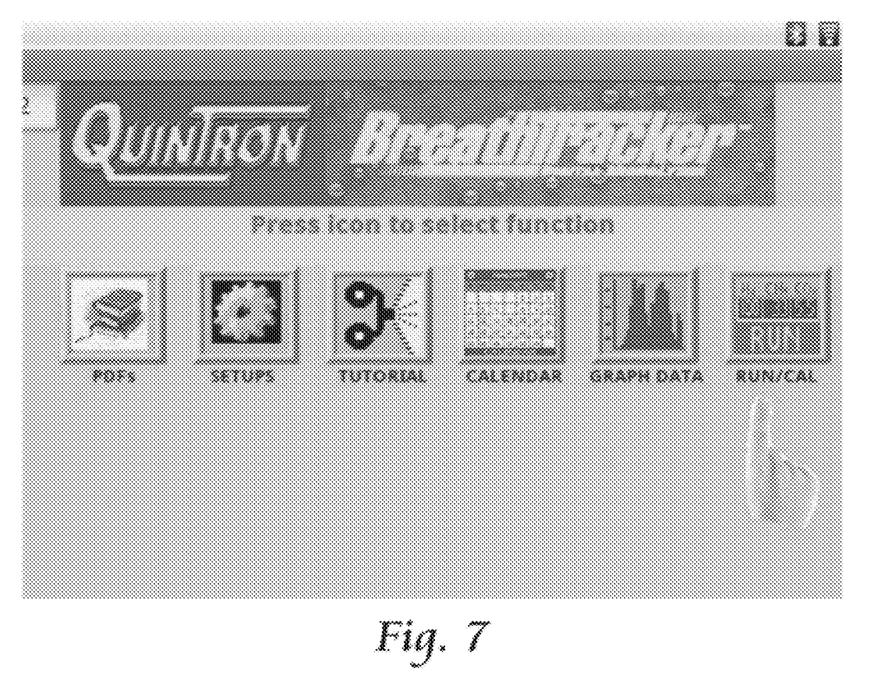
FIG. 7 shows selection of a run/calibration mode from the main screen.
Figure 8:
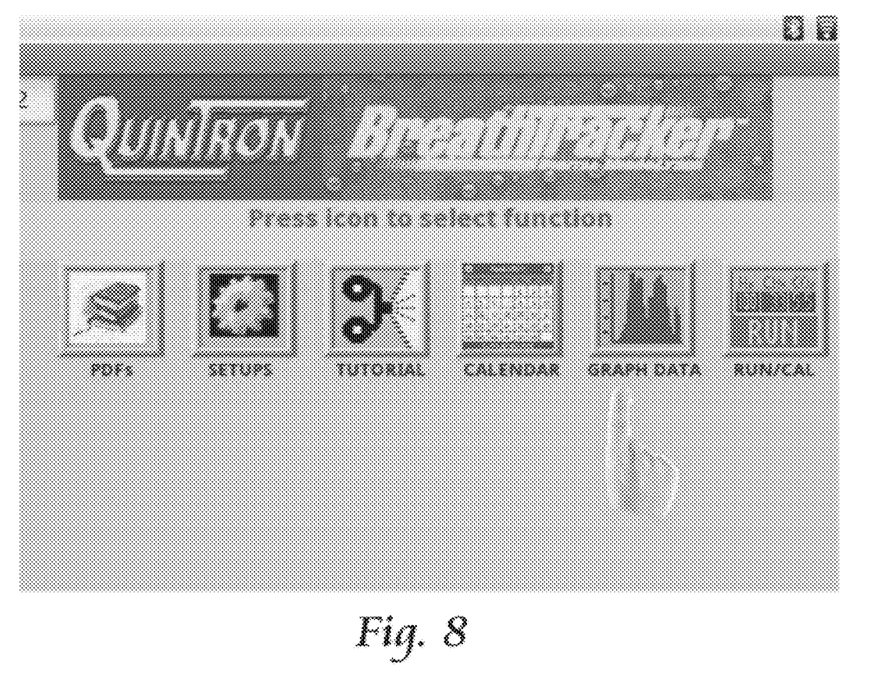
FIG. 8 shows selection of a graph data function from the main screen.
Figure 9:
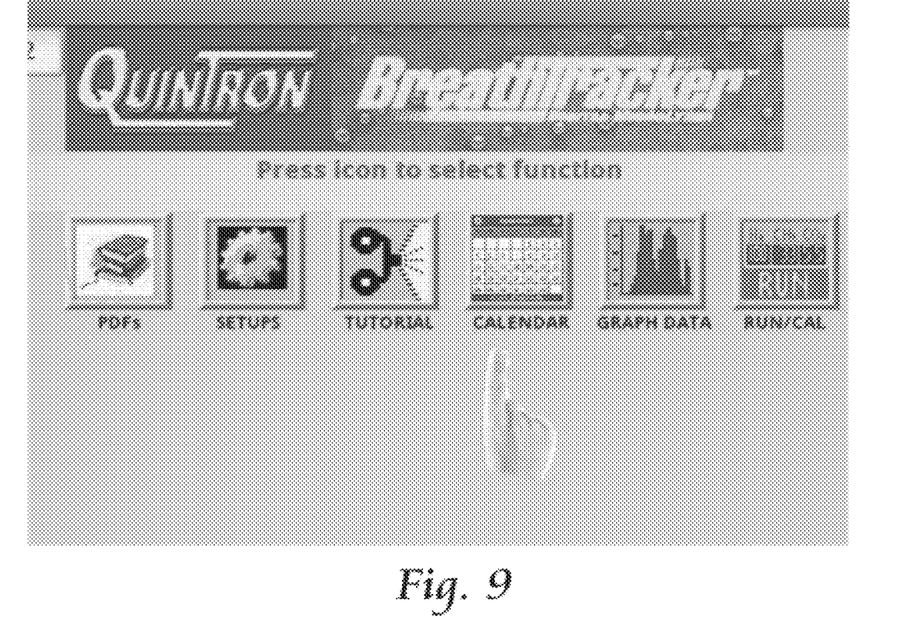
FIG. 9 shows selection of a calendar function from the main screen.

Referring now to FIG. 3, an exemplary screen shot of a user interface showing a main screen is shown. Several modes can be selected, as shown in FIG. 7 (run/calibration mode), FIG. 8, (data graphing function), FIG. 9, calendar function, FIG. 11, PDF manual selection function.

Figure 4:
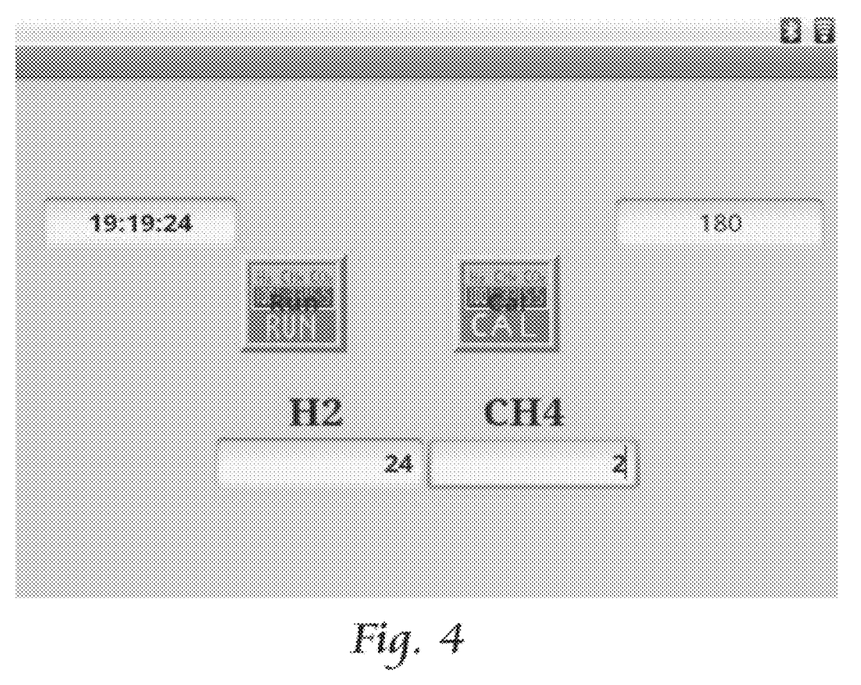
FIG. 4 is a user interface showing run and calibration modes for $H_2$, $CH_4$, and $CO_2$.

Referring now to FIG. 4, an exemplary user interface showing run and calibration modes for $H_2$, $CH_4$, and $CO_2$ is shown. These tests can be particularly useful in breath testing machines, for which the present invention is well suited.

For example, as shown in table 1 below, several protocols can be implemented using $H_2$, $CH_4$, and $CO_2$ results:

TABLE 1

GENERAL GUIDELINES FOR CARBOHYDRATE BREATH HYDROGEN & METHANE TESTING

| CHALLENGE | DOSE | SAMPLING INTERVALS | INTERPRETING RESULTS |
| --- | --- | --- | --- |
| LACTOSE | Lactose: 1 g/kg body Weight up to 25 g dissolved in 6-8 oz. (250 ml) of water. | Standard: Baseline (0), 60, 120, 180 minutes after the sugar has been ingested. (4 Samples Total) | POSITIVE: Breath H2 level increase of at least 20 ppm over the lowest preceding value within the test period; Breath CH4 level increases be at least 12 ppm over the baseline within the test period: combined increase of at least 15 ppm H2/CH4 within the test period. |
| FRUCTOSE | Fructose: 1 g/kg body weight up to 25 g dissolved in 6-8 oz. (250 ml) of water. | Standard: Baseline (0), 60 120, 180 minutes after the sugar has been ingested. (4 Samples Total) | POSITIVE: Breath H2 level increase of at least 20 ppm over the lowest preceding value within the test period: Breath CH4 level increases be at least 12 ppm over the baseline within the test period: combined increase of at least 15 ppm H2/CH2 wtihin the test period. (Note: Fructose malabsorption is reduced by concomitant glucose or sucrose intake.) |
| SMALL INTESTINAL BACTERIAL OVERGROWTH (S.I.B.O.) | Lactulose: 10 g dissolved in 6-8 OZ. of water, 10 g (15 ml) lactulose syrup Glucose: 70-100 g dissolved in 8 OZ. of water, 1 g/kg body weight. | Standard: (H/CH4 baseline may be elevated) Baseline (0), then every 20 minutes for 3 hours after sugar has been ingested. (10 Samples Total) | POSITIVE: Lactulose: Biphasic pattern in breath H2/CH4 levels two peaks with an early increase of at least 20 ppm within the first 2 hours, followed by a much larger increase. POSITIVE: Glucose: An early increase of at least 12 ppm breath H2 and/or CH4 over the baseline value. No late peak of H2 or CH4. |
| SUCROSE | Sucrose: 2 g/kg body weight up to 50 g dissolved in 6-8 oz. (250 ml) of water. | Standard: Baseline (0), then every 30 minutes for 3 hours after sugar has been ingested. (7 Samples Total) | POSITIVE: Breath H2 level increase of at least 20 ppm over the lowest preceding value within the test period. Breath CH4 level increases be at least 12 ppm over the baseline within the test period; combined increase of at least 15 ppm H2/CH4 within the test period. |
| D-XYLOSE | d-Xylose: 1 g/kg body weight up to 25 g dissolved in 6-8 oz. (250 ml) of water. | Standard: Baseline (0), then every 20 minutes for 3 hours after sugar has been ingested. (10 Samples Total) | d-Xylose: Increase of either H2 and/or CH4 levels of 20 ppm within 40-60 minutes suggest bacterial overgrowth. An increase >60 min suggests impairment of intestinal transport capacity. |
| SORBITOL | Sorbitol: 0.25-0.50 g/kg body weight up to 10 g dissolved in 6-8 oz. water. | Standard: Baseline (0), then every 30 minutes for 3 hours after sugar has been ingested. (7 Samples Total) | Breath H2 level increase after 60 min is NORMAL. An increase of over 30 ppm with cramps indicates sensitivity to sorbitol. |

TABLE 1-continued

GENERAL GUIDELINES FOR CARBOHYDRATE BREATH HYDROGEN & METHANE TESTING

| CHALLENGE | DOSE | SAMPLING INTERVALS | INTERPRETING RESULTS |
|---|---|---|---|
| INTESTINAL TRANSIT TIME | Lactulose: 0.50 g/kg body weight up to 10 g dissolved in 6-8 oz of water, 10 g (15 ml lactulose syrup) | Standard: Beginning 40 minutes after challenge dose, sample every 10 minutes until the H2 and/or CH4 corrected value rises 3 ppm over the previous level for at least 3 successive time intervals. Reduce sampling to every 20 minutes after 2 hours. | Normal mean for Lactulose testing: 70-75 minutes. Note: Lactose shortens intestinal transit time compared to other tests. |

Figure 5:
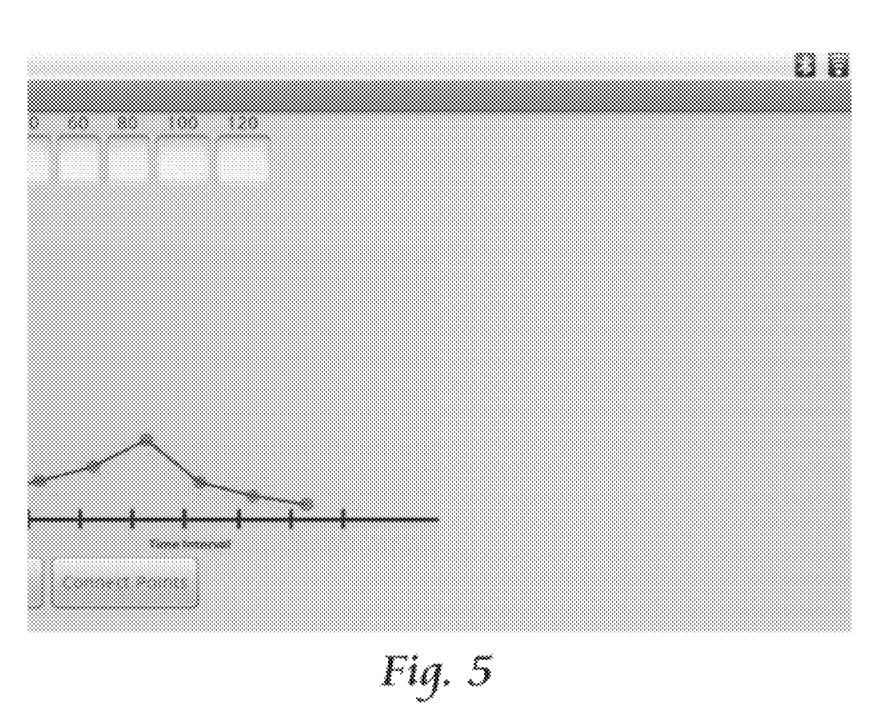
FIG. 5 shows graphing options.

FIG. 5 shows graphing options. For example, results of $H_2$, $CH_4$, and $CO_2$ can be charted over time, and analyzed in that manner by the present machine.

Figure 6:
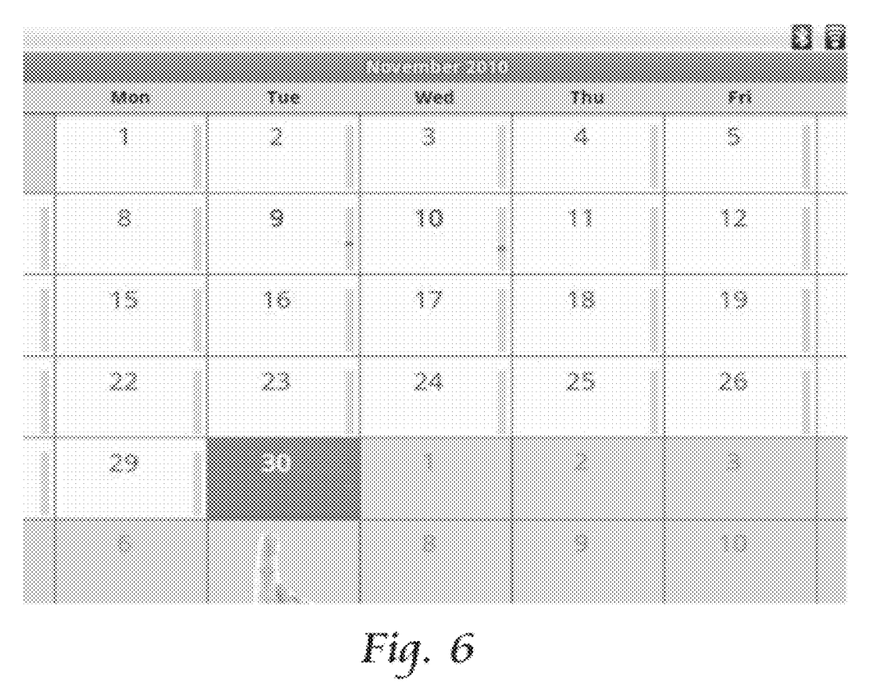
FIG. 6 shows calendar options.

Referring now to FIG. 6, calendar options are also optionally provided. In this manner, reminders about testing frequency and software updates can be provided.

Referring now to FIG. 7, a run/calibration mode from the main screen is available to ensure data integrity.

Figure 10:
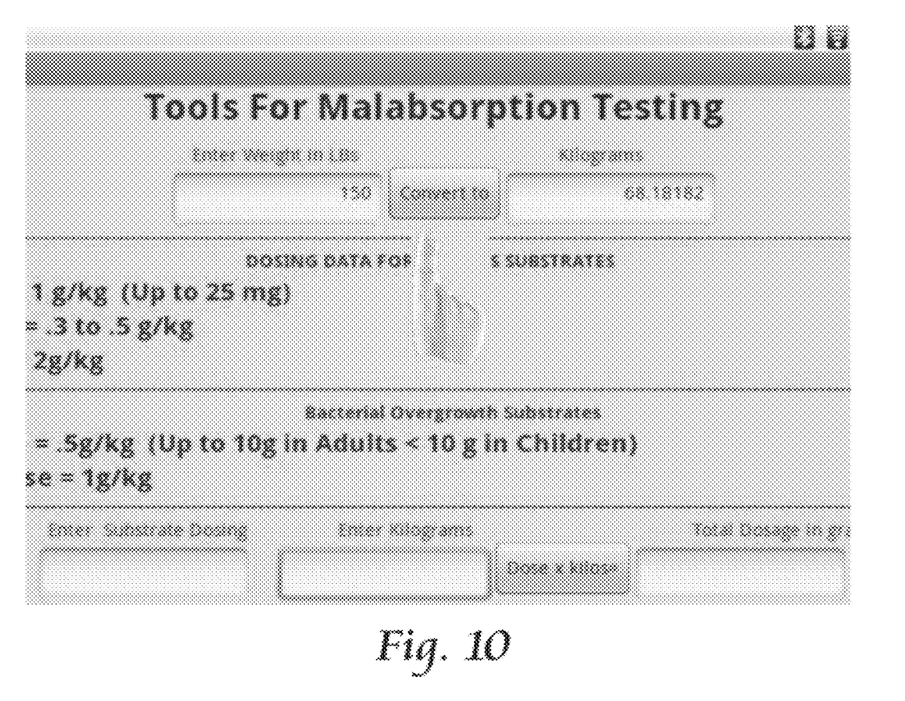
FIG. 10 shows tools for testing, including dosing data and bacterial overgrowth substrate.

Recommendations, such as shown in FIG. 10, can be provided, by which tools for malabsorption testing, including dosing data and bacterial overgrowth substrate can be given.

Figure 11:
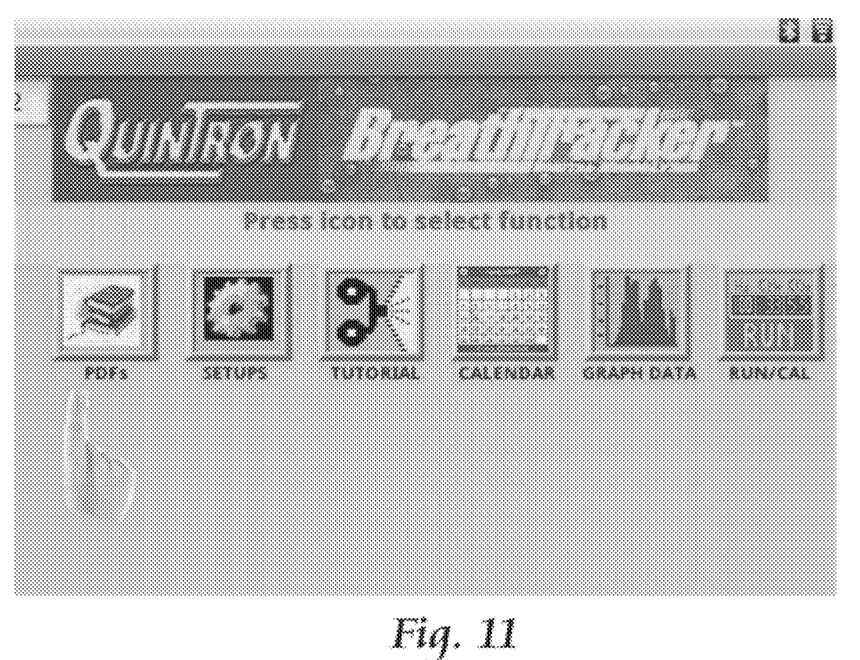
FIG. 11 shows selection of PDF format instruction manuals carried onboard, such as catalogs, methane test books, and other supplier selected documentation related to the breath testing machine.
Figure 12:
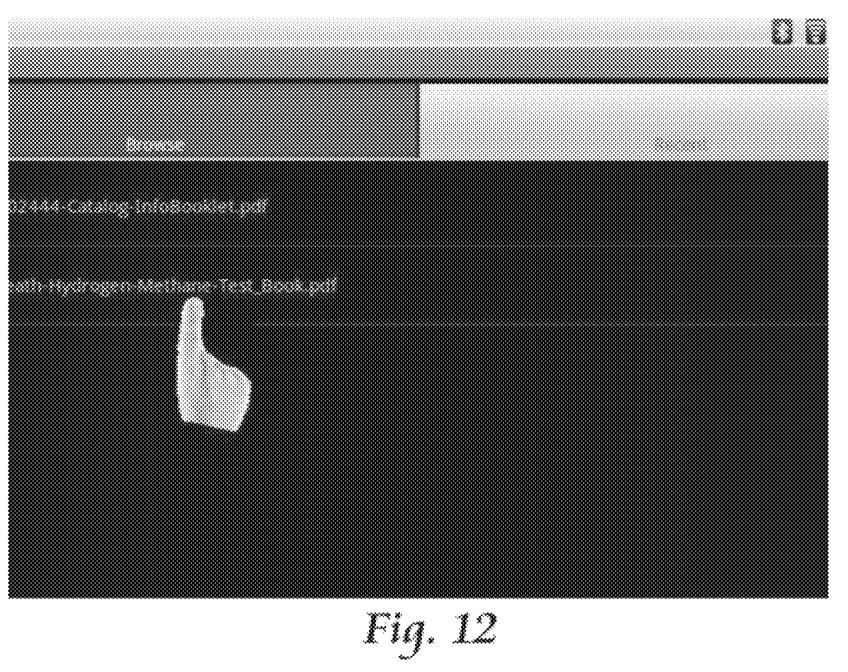
FIG. 12 shows an example of types of PDF format instruction manuals carried onboard, such as catalogs, methane test books, and other supplier selected documentation related to the breath testing machine.
Figure 13:
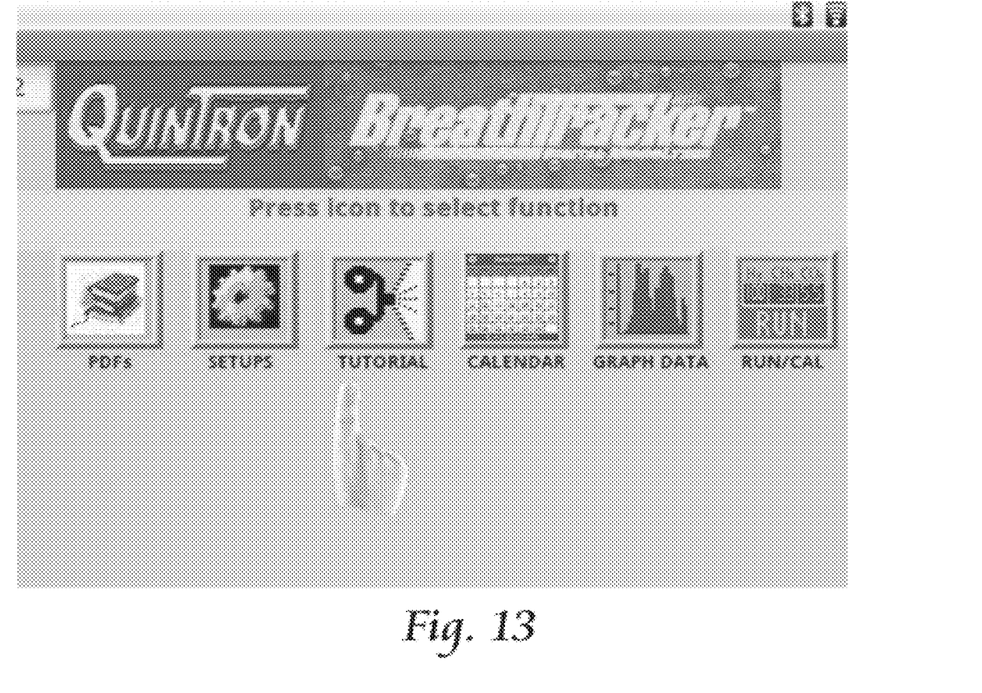
FIG. 13 is selection of a tutorial function, selection of which reference tutorial videos carried onboard.

Referring now to FIG. 11, the machine can carry, on board, and in electronic format, instruction manuals, such as PDF format instruction manuals carried onboard, such as catalogs, methane test books, and other supplier selected documentation related to the breath testing machine. The machine can also carry on board, such as shown in FIG. 13, a tutorial function, selection of which reference tutorial videos carried onboard. This is beneficial for training purposes should new users be introduced to the machine.

All of the patient data can be downloaded and uploaded remotely to and from the machine, and likewise the training and instructional data can be shared across Bluetooth and wifi connections with those connected to the machine.

In accordance with the present invention, a testing apparatus is provided with on-board "Instruction Manual" tutorials incorporated in a display device installed in the device. Alternatively, on-board instructional videos can be added to various objects or processes requiring instructions. Exemplary uses of the present invention also include video displays in automobiles, which often incorporate combined GPS-DVD-CD-AM FM Radio consoles. Such video capabilities can be added to include commercially available video applications such as which could include a "flash player", HTML 5, MPEG, WMV, AVI, DIVX or other video player. In this embodiment, the present invention can be used to display video demonstrating the operation of certain devices in the auto such as, the location and method of changing the spare tire, and other pertinent demos related to operation of the vehicle or devices within the vehicle (setting the clock, etc). It could also include instruction manuals for repair and servicing.

In another alternate embodiment of the present invention, video capability is added to machines such as computer printers, fax machines, and copiers often have lcd graphic displays for simple sequential operations of the devices. Adding video player functions would enhance the ability to provide more comprehensive instructions in the operation of the device.

In another alternate embodiment of the present invention, scientific and laboratory instruments are provided with "In Service" Instructions directly on those devices (in the form of video), ensuring proper training for successive users. These "In Service" instructions may result in significant savings for the manufacturer, by eliminating requirements for training personnel to travel to user sites to provide "In Service" training.

In another alternate embodiment of the present invention, inclusion of graphic display devices are provided to allow visual "Instruction Manuals" in many other types of vehicles such as snowmobiles, atvs, lawnmowers, motorcycles and other vehicles, to provide instruction on incorporated DVD players, televisions, stereo equipment.

The device utilizes a tablet computer a User Interface and Control Device for an Instrument. A primary reason for this approach is that such devices have many built-in functions that can be utilized in providing an instrument with extremely diverse utility. Built-in capability to read PDF files, show video files, connect to wifi for email and Internet access, bluetooth communications for control functions, programmability enabling incorporation of the designers proprietary functions and design are typical of the capability of such devices. Additionally the flexibility of this concept allows simple modification of the User Interface with additional push-button controls and displays as well as other control and information access. The Control Function of such a system can also be modified simply. Independently designing an instrument with all this functionality is certainly attainable; however design time and expense would most likely be long and excessive.

An instrument manufactured with Built-in video operation could prove invaluable where in-service training is available on the instrument itself. Additional Built-in pdf Reader capability would provide reference materials for training, supplies information, and part numbers, patient diet instructions and pretest options and requirements, prescription drug instructions, dosing instructions and tools if the test requires drug or other substrate ingestion or inoculation. Communications capabilities provide additional power in such a device. Wifi and Bluetooth communications and existing or available ethernet communications can provide a rich variety of options for communicating test results, patient appointment information, consultation options and general information sharing in many forms . . . SMS, MMS, Email, etc. Powerful calendars and other utility software designed as applications for the Android operating system (or other operating systems, such as Windows, Chrome, etc; if the primary system is an alternative O.S.) can provide an additional source of enhanced functionality to the Instrument. This design concept applies additional instrument design and control flexibility.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. A breath testing apparatus comprising: an intake for receiving an air sample; a mechanism for analyzing said sample; a mechanism for displaying results of said sample; said mechanism for displaying results of said sample comprising a graphical user interface menu comprising, a mechanism for displaying a tutorial of how to use said breath testing apparatus; a setup menu, a video training tutorial carried on said breath testing and sampling apparatus, a calendar function, a graph data function, a run/calibrate function; and a mechanism for storing, uploading and analyzing patient data;

said run/calibrate function further comprising an interface showing run and calibration modes for $H_2$, $CH_4$, and $CO_2$;

said mechanism for displaying results of said sample further providing recommendations for malabsorption and bacterial overgrowth testing, including dosing data and substrates;

said mechanism for displaying results of said sample further providing instructions for steps to be performed separate and apart from the apparatus, said instructions comprising patient diet instructions.

* * * * *